(12) United States Patent
Kramer et al.

(10) Patent No.: US 10,246,546 B2
(45) Date of Patent: Apr. 2, 2019

(54) POLYMER CONTAINING SILANE GROUPS

(71) Applicant: SIKA TECHNOLOGY AG, Baar (CH)

(72) Inventors: Andreas Kramer, Zürich (CH); Urs Burckhardt, Zürich (CH)

(73) Assignee: SIKA TECHNOLOGY AG, Baar (CH)

( * ) Notice: Subject to any disclaimer, the term of this patent is extended or adjusted under 35 U.S.C. 154(b) by 0 days.

(21) Appl. No.: 15/522,004

(22) PCT Filed: Nov. 23, 2015

(86) PCT No.: PCT/EP2015/077374
§ 371 (c)(1),
(2) Date: Apr. 26, 2017

(87) PCT Pub. No.: WO2016/083310
PCT Pub. Date: Jun. 2, 2016

(65) Prior Publication Data
US 2017/0320997 A1    Nov. 9, 2017

(30) Foreign Application Priority Data

Nov. 24, 2014    (EP) .................................... 14194594

(51) Int. Cl.
| | | |
|---|---|---|
| *C08G 18/28* | (2006.01) |
| *C07F 7/18* | (2006.01) |
| *C08G 18/48* | (2006.01) |
| *C08G 18/10* | (2006.01) |
| *C08G 18/75* | (2006.01) |
| *C08G 18/34* | (2006.01) |
| *C08G 18/66* | (2006.01) |

(52) U.S. Cl.
CPC .......... *C08G 18/289* (2013.01); *C07F 7/1804* (2013.01); *C08G 18/10* (2013.01); *C08G 18/341* (2013.01); *C08G 18/4825* (2013.01); *C08G 18/4866* (2013.01); *C08G 18/6692* (2013.01); *C08G 18/755* (2013.01)

(58) Field of Classification Search
CPC ..................................................... C08L 101/10
See application file for complete search history.

(56) References Cited

U.S. PATENT DOCUMENTS

| | | |
|---|---|---|
| 5,587,502 A | 12/1996 | Moren et al. |
| 2008/0221238 A1 | 9/2008 | Su et al. |

FOREIGN PATENT DOCUMENTS

| | | |
|---|---|---|
| WO | 2013/174891 A2 | 11/2013 |
| WO | 2013/174892 A1 | 11/2013 |

OTHER PUBLICATIONS

Huang (Analytical Sciences (2003) 19(10) 1391-1394).*
Feb. 11, 2016 International Search Report issued in International Patent Application No. PCT/EP2015/077374.

* cited by examiner

*Primary Examiner* — Kuo Liang Peng
(74) *Attorney, Agent, or Firm* — Oliff PLC

(57) ABSTRACT

A polymer containing silane groups, a method for synthesizing same, and curable compositions including the polymer. The polymer containing silane groups has a very long shelf life and cures quickly with moisture. The polymer is suitable as an elastic adhesive or sealant or coating that can be applied at room temperature and has good heat resistance, or as a hot melt adhesive.

15 Claims, No Drawings

POLYMER CONTAINING SILANE GROUPS

TECHNICAL FIELD

The invention relates to polymers containing silane groups and to the use thereof in curable compositions usable especially for bonding, sealing or coating of construction or industrial products.

STATE OF THE ART

Polymers containing silane groups, also referred to as "silane-functional polymers" or "silane-modified polymers" (SMP) or "silane-terminated polymers" (STP), have been used successfully for some time as binders in moisture-curing compositions which find use especially as elastic adhesives, sealants or coatings in the construction and manufacturing industry.

An easily implementable and commercially attractive route to polymers containing silane groups leads via polyurethane polymers containing isocyanate groups, which are reacted with suitable organosilanes. Aminosilanes are usually used for this purpose. However, polymers thus prepared, because of the urea groups formed in the reaction with the aminosilane, typically have high viscosities and/or limited thermal stability. Better properties in relation to viscosity and thermal stability are possessed by polymers containing silane groups in which the silane groups are bonded to the polymer via urethane groups rather than urea groups. Systems of this kind are known in the form of reaction products of polyols and isocyanatosilanes. However, this route is only of limited commercial interest, since isocyanatosilanes are costly, have a short shelf life and are highly toxic.

In principle, the converse route to polymers containing silane groups and having urethane bonds appears more attractive, namely via the reaction of polyurethane polymers containing isocyanate groups with hydroxysilanes. However, there have barely been any descriptions of such polymers to date. The reason for this is that the preparation of suitable hydroxysilanes usually presents difficulties because they have a tendency to self-condensation owing to a rapid reaction of the hydroxyl group with the silane group and are therefore frequently very impure and/or have a short shelf life.

U.S. Pat. No. 5,587,502 discloses hydroxysilanes obtained by reacting aminosilanes with cyclic alkylene carbonates, and polymers containing silane groups that emanate therefrom. However, these polymers containing silane groups have inadequate thermal stabilities.

WO 2013/174891 and WO 2013/174892 disclose hydroxysilanes obtained by reacting aminosilanes with lactones or by reacting epoxysilanes with secondary amines, and polymers containing silane groups that emanate therefrom. However, the polymers containing silane groups disclosed are still in need of improvement with regard to storage stability.

SUMMARY OF THE INVENTION

It is therefore an object of the present invention to provide a polymer containing silane groups which has a low viscosity and good storage stability, crosslinks rapidly with moisture, and has good thermal stability in the cured state.

It has been found that, surprisingly, this object is achieved by a polymer as claimed in claim 1. The polymer is preparable in high purity in a simple process from raw materials of good commercial availability. It is very storage-stable, surprisingly even with the very reactive methoxysilane groups, and cures rapidly with moisture to give a nontacky elastic material having good thermal stability.

Further aspects of the invention are the subject of further independent claims. Particularly preferred embodiments of the invention are the subject of the dependent claims.

WAYS OF EXECUTING THE INVENTION

The invention provides a polymer having end groups of the formula (I)

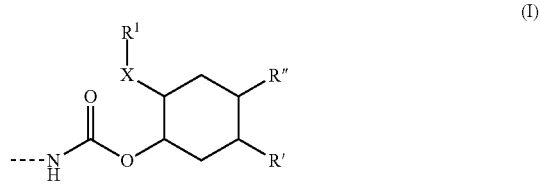

where
either R' is a radical of the formula (II) and R" is a hydrogen radical
or R' is a hydrogen radical and R" is a radical of the formula (II);

$R^1$ is a hydrocarbyl radical which has 1 to 18 carbon atoms and optionally has heteroatoms in the form of ether oxygen, ester oxygen, thioether sulfur or tertiary amine nitrogen;
$R^2$ is a linear or branched alkylene or cycloalkylene radical having 1 to 20 carbon atoms, optionally having aromatic components, and optionally having one or more heteroatoms;
$R^3$ is an alkyl radical having 1 to 8 carbon atoms;
$R^4$ is an aliphatic or cycloaliphatic or arylaliphatic hydrocarbyl radical which has 1 to 12 carbon atoms and optionally has one or two ether oxygens;
X is O or S; and
n is 0 or 1 or 2.

In the present document, the term "alkoxysilane group" or "silane group" for short refers to a silyl group which is bonded to an organic radical and has one to three, especially two or three, hydrolyzable alkoxy radicals on the silicon atom. A "methoxysilane group" refers to a silane group having exclusively methoxy radicals as alkoxy radicals. An "ethoxysilane group" refers to a silane group having exclusively ethoxy radicals as alkoxy radicals.

The term "alkoxysilane" or "silane" for short refers to an organic compound having at least one silane group.

"Hydroxysilane", "epoxysilane", "isocyanatosilane", "aminosilane" and "mercaptosilane" refer respectively to silanes having one or more hydroxyl, epoxy, isocyanato, amino and mercapto groups on the organic radical in addition to the silane group.

Substance names beginning with "poly", such as polyol or polyisocyanate, refer to substances which, in a formal sense, contain two or more functional groups that occur in their name per molecule.

"Molecular weight" in the present document refers to the molar mass (in grams per mole) of a molecule. "Average molecular weight" is understood to mean the number average $M_n$ of an oligomeric or polymeric mixture of molecules, which is typically determined by means of gel permeation chromatography (GPC) against polystyrene as standard.

"Storage-stable" or "storable" refers to a substance or composition when it can be stored at room temperature in a suitable container over a prolonged period, typically at least 3 months up to 6 months or more, without undergoing any change to a degree of relevance for its use in its application or use properties, especially in the viscosity and the crosslinking rate, as a result of the storage. The term "viscosity" refers in the present document to the dynamic viscosity or shear viscosity which is determined by the ratio between the shear stress and the shear rate (shear rate gradient) and is determined as described in the working examples.

A dotted line in the formulae in this document in each case represents the bond between a substituent and the corresponding remainder of the molecule. "Room temperature" refers to a temperature of 23° C.

The end groups of the formula (I) correspond either to the formula (Ia) or to the formula (Ib).

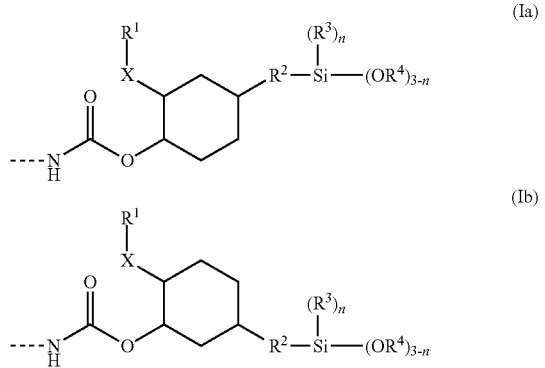

In the formulae (Ia) and (Ib), $R^1$, $R^2$, $R^3$, $R^4$, X and n have the definitions already given above.

In one embodiment of the invention, $R^1$ is an aromatic hydrocarbyl radical which has 6 to 18 carbon atoms, is optionally substituted and optionally has heteroatoms in the form of ether oxygen, ester oxygen, thioether sulfur or tertiary amine nitrogen, and is preferably 4-tert-butylphenyl, 4-nonylphenyl, 4-dodecylphenyl, 2,3-dimethylphenyl, 2,4-dimethylphenyl or 2,5-dimethylphenyl.

In a preferred embodiment of the invention, $R^1$ is an aliphatic or cycloaliphatic or arylaliphatic hydrocarbyl radical which has 1 to 18 carbon atoms and optionally has heteroatoms in the form of ether oxygen, ester oxygen, thioether sulfur or tertiary amine nitrogen. These polymers containing silane groups are advantageous for toxicological reasons.

More preferably, $R^1$ is an aliphatic or cycloaliphatic or arylaliphatic hydrocarbyl radical which has 1 to 12 and especially 1 to 8 carbon atoms and optionally has one or two ether oxygens.

Most preferably, $R^1$ is a methyl radical or an ethyl radical.

Preferably, $R^2$ is an alkylene radical having 1 to 6 carbon atoms, especially a 1,2-ethylene radical.

Preferably, $R^3$ is a methyl radical.

Preferably, $R^4$ is a methyl radical or an ethyl radical. These end groups of the formula (I) are particularly reactive.

$R^4$ is especially a methyl radical. These end groups of the formula (I) are particularly reactive with moisture, which means that the polymer containing silane groups cures particularly rapidly.

$R^4$ is also especially an ethyl radical. These end groups of the formula (I) do not eliminate any methanol as they cure, which is advantageous for toxicological reasons.

Preferably, X is O. These polymers containing silane groups are advantageous in terms of odor.

More preferably, X is O and $R^1$ and $R^4$ are the same radical, and are especially each a methyl radical or are each an ethyl radical.

Preferably, n is 0 or 1, especially 0. These end groups of the formula (I) are hydrolyzed particularly rapidly on contact with moisture and give rise to polymers containing silane groups that have particularly good mechanical properties.

The preferred end groups of the formula (I) are obtainable particularly efficiently and preparable in particularly pure quality.

Preferably, the polymer has an average functionality in the range from 1.3 to 4, especially 1.5 to 3, more preferably 1.7 to 2.8, in relation to end groups of the formula (I).

Preferably, the polymer having end groups of the formula (I) has an average molecular weight in the range from 1'000 to 30'000 g/mol, preferably 2'000 to 25'000 g/mol, more preferably 3'000 to 20'000 g/mol.

Such a polymer enables good mechanical properties, especially high extensibility.

A preferred polymer having end groups of the formula (I) is a polyether containing silane groups which is liquid at room temperature. It preferably has a majority of oxyalkylene units, especially 1,2-oxypropylene units. The majority of its end groups of the formula (I) are preferably bonded to cycloaliphatic or aromatic radicals, especially to radicals derived from isophorone diisocyanate (IPDI) or from tolylene 2,4- and/or 2,6-diisocyanate (TDI). Such a polymer has a low viscosity and enables good elastic properties. It is especially suitable as a binder in adhesives or sealants or coatings that are applicable at room temperature. Such a polymer is preferably free of isocyanate groups. With end groups of the formula (I) bonded to cycloaliphatic radicals, it is particularly light-stable.

A further preferred polymer having end groups of the formula (I) is a polyester which is solid at room temperature and/or a polycarbonate which is solid at room temperature, especially a polyester. The majority of its end groups of the formula (I) are bonded to cycloaliphatic or aromatic radicals, preferably to radicals derived from isophorone diisocyanate (IPDI) or from diphenylmethane 4,4', 2,4'- and/or 2,2'-diisocyanate (MDI). Such a polymer is especially suitable as a binder in adhesives applicable while hot, called hotmelt adhesives. Such a polymer may, as well as end groups of the formula (I), also contain isocyanate groups. With end groups of the formula (I) bonded to cycloaliphatic radicals, it is particularly light-stable.

The invention further provides a process for preparing a polymer having end groups of the formula (I) by reacting at least one hydroxysilane of the formula (III) with at least one polyurethane polymer containing isocyanate groups.

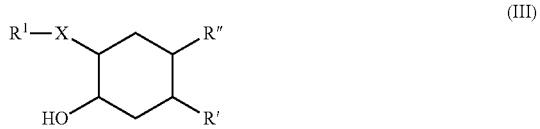

In the formula (III), $R^1$, R', R" and X have the definitions already given.

The hydroxysilane of the formula (III) corresponds either to the formula (IIIa) or to the formula (IIIb).

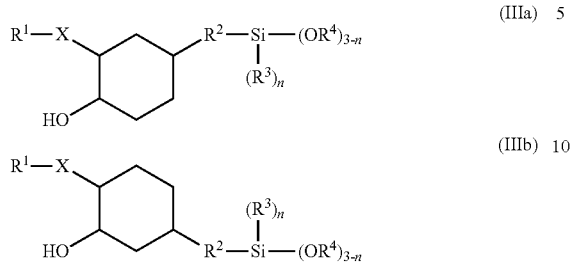

(IIIa)

(IIIb)

In the formulae (IIIa) and (IIIb), $R^1$, $R^2$, $R^3$, $R^4$, X and n have the definitions already given above.

The formulae (IIIa) and (IIIb) include all the diastereomers possible for the particular structure.

The reaction is preferably conducted with exclusion of moisture at a temperature in the range from 20 to 160° C. Optionally, a catalyst is used, especially a tertiary amine or a metal compound, especially a bismuth(III), zinc(II) zirconium(IV) or tin(II) compound, or an organotin(IV) compound. The hydroxysilane of the formula (III) is preferably used in a superstoichiometric or stoichiometric ratio relative to the isocyanate groups, such that a polymer having end groups of the formula (I) which is free of isocyanate groups is obtained. More particularly, an OH/NCO ratio in the range from 1 to 1.25 is employed. The reaction is advantageously monitored by measuring the isocyanate content of the polymer obtained, for example by means of IR spectroscopy.

If the hydroxysilane of the formula (III) is used in a substoichiometric amount, the polymer obtained will additionally contain isocyanate groups as well as end groups of the formula (I). Such a polymer is preferably prepared by using an OH/NCO ratio in the range from 0.1 to 0.9, more preferably 0.2 to 0.8, especially 0.3 to 0.7. The polymer obtained has a distinctly reduced content of monomeric diisocyanate compared to the polyurethane polymer having isocyanate groups which is used, which is advantageous for toxicological reasons.

A suitable polyurethane polymer containing isocyanate groups is especially obtained from the reaction of at least one polyol with a superstoichiometric amount of at least one diisocyanate. The reaction is preferably conducted with exclusion of moisture at a temperature in the range from 50 to 160° C., optionally in the presence of suitable catalysts. More particularly, the excess of diisocyanate is chosen so as to leave, in the resulting polymer after the conversion of all hydroxyl groups, a content of free isocyanate groups of 0.1% to 5% by weight, preferably 0.2% to 4% by weight, more preferably 0.3% to 3% by weight, based on the overall polymer. Optionally, the polyurethane polymer can be prepared with additional use of plasticizers, in which case the plasticizers used do not contain any groups reactive toward isocyanates.

Suitable polyols for are especially the following commercial polyols or any desired mixtures thereof:
  polyether polyols, especially polyoxyalkylenediols and/or polyoxyalkylenetriols, especially polymerization products of ethylene oxide or 1,2-propylene oxide or 1,2- or 2,3-butylene oxide or oxetane or tetrahydrofuran or mixtures thereof, where these may have been polymerized with the aid of a starter molecule having two or more active hydrogen atoms, especially a starter molecule such as water, ammonia or a compound having a plurality of OH or NH groups, for example ethane-1,2-diol, propane-1,2- or 1,3-diol, neopentyl glycol, diethylene glycol, triethylene glycol, the isomeric dipropylene glycols or tripropylene glycols, the isomeric butanediols, pentanediols, hexanediols, heptanediols, octanediols, nonanediols, decanediols, undecanediols, cyclohexane-1,3- or -1,4-dimethanol, bisphenol A, hydrogenated bisphenol A, 1,1,1-trimethylolethane, 1,1,1-trimethylolpropane, glycerol or aniline, or mixtures of the aforementioned compounds. Likewise suitable are polyether polyols with polymer particles dispersed therein, especially those comprising styrene-acrylonitrile particles (SAN) or acrylonitrile-methyl methacrylate particles. Preferred polyether polyols are polyoxypropylenediols and/or polyoxypropylenetriols, or what are called ethylene oxide-terminated (EO-endcapped) polyoxypropylenediols or -triols. The latter are polyoxyethylene-polyoxypropylene copolyols, which are especially obtained by further alkoxylating polyoxypropylenediols or -triols with ethylene oxide on conclusion of the polypropoxylation reaction, as a result of which they ultimately have primary hydroxyl groups.

Preferred polyether polyols have a degree of saturation of less than 0.02 meq/g, especially less than 0.01 meq/g.

Polyester polyols, also called oligoesterols, prepared by known processes, especially the polycondensation of hydroxycarboxylic acids or the polycondensation of aliphatic and/or aromatic polycarboxylic acids with di- or polyhydric alcohols.

Especially suitable polyester polyols are those prepared from di- to trihydric, especially dihydric, alcohols, for example ethylene glycol, diethylene glycol, propylene glycol, dipropylene glycol, neopentyl glycol, butane-1,4-diol, pentane-1,5-diol, 3-methylhexane-1,5-diol, hexane-1,6-diol, octane-1,8-diol, decane-1,10-diol, dodecane-1,12-diol, 1,12-hydroxystearyl alcohol, cyclohexane-1,4-dimethanol, dimer fatty acid diol (dimer diol), neopentyl glycol hydroxypivalate, glycerol, 1,1,1-trimethylolpropane or mixtures of the aforementioned alcohols, with organic di- or tricarboxylic acids, especially dicarboxylic acids, or the anhydrides or esters thereof, for example succinic acid, glutaric acid, adipic acid, trimethyladipic acid, suberic acid, azelaic acid, sebacic acid, dodecanedicarboxylic acid, maleic acid, fumaric acid, dimer fatty acid, phthalic acid, phthalic anhydride, isophthalic acid, terephthalic acid, dimethyl terephthalate, hexahydrophthalic acid, trimellitic acid and trimellitic anhydride, or mixtures of the aforementioned acids, and also polyester polyols formed from lactones, for example from ε-caprolactone, and starters such as the aforementioned di- or trihydric alcohols.

Particularly suitable polyester polyols are polyester diols.

Polycarbonate polyols as obtainable by reaction, for example, of the abovementioned alcohols—used to form the polyester polyols—with dialkyl carbonates, diaryl carbonates or phosgene.

Block copolymers bearing at least two hydroxyl groups and having at least two different blocks having polyether, polyester and/or polycarbonate structure of the type described above, especially polyether polyester polyols.

Polyacrylate- and polymethacrylatepolyols.

Polyhydroxy-functional fats and oils, for example natural fats and oils, especially castor oil; or what are called oleochemical polyols, obtained by chemical modification of natural fats and oils, for example the epoxy polyesters or epoxy polyethers obtained by epoxidation of unsaturated oils and subsequent ring opening with carboxylic acids or alcohols, or polyols obtained by hydroformylation and hydrogenation of unsaturated oils; or polyols obtained from natural fats and oils by degradation processes such as alcoholysis or ozonolysis and subsequent chemical linkage, for example by transesterification or dimerization, of the degradation products or derivatives thereof thus obtained. Suitable degradation products of natural fats and oils are especially fatty acids and fatty alcohols, and also fatty acid esters, especially the methyl esters (FAME), which can be derivatized, for example, by hydroformylation and hydrogenation to give hydroxy fatty acid esters.

Polyhydrocarbonpolyols, also called oligohydrocarbonols, for example polyhydroxy-functional polyolefins, polyisobutylenes, polyisoprenes; polyhydroxy-functional ethylene-propylene, ethylene-butylene or ethylene-propylene-diene copolymers, as produced, for example, by Kraton Polymers; polyhydroxy-functional polymers of dienes, especially of 1,3-butadiene, which may also be prepared from anionic polymerization in particular; polyhydroxy-functional copolymers of dienes such as 1,3-butadiene or diene mixtures and vinyl monomers such as styrene, acrylonitrile, vinyl chloride, vinyl acetate, vinyl alcohol, isobutylene and isoprene, for example polyhydroxy-functional acrylonitrile/butadiene copolymers, as producible, for example, from epoxides or amino alcohols and carboxyl-terminated acrylonitrile/butadiene copolymers (commercially available, for example, under the Hypro® (formerly Hycar®) CTBN and CTBNX and ETBN name from Nanoresins AG, Germany, or Emerald Performance Materials LLC); and hydrogenated polyhydroxy-functional polymers or copolymers of dienes.

Preferred polyols are polyether polyols, polyester polyols or polycarbonate polyols.

Particular preference is given to polyoxypropylenediols that are liquid at room temperature and have an average molecular weight in the range from 1'000 to 20'000 g/mol, preferably from 2'000 to 15'000 g/mol. These polyols are particularly suitable for the preparation of polymers having end groups of the formula (I) that are liquid at room temperature.

Particular preference is further given to amorphous or semicrystalline or crystalline polyester polyols or polycarbonate polyols that are solid at room temperature, especially polyester diols having an average molecular weight in the range from 1'500 to 15'000 g/mol, preferably 1'500 to 8000 g/mol, especially 2'000 to 5'500 g/mol, especially crystalline or semicrystalline adipic acid/hexanediol polyesters or dodecanedicarboxylic acid/hexanediol polyesters. These polyols are particularly suitable for the preparation of polymers having end groups of the formula (I) that are solid at room temperature.

Suitable diisocyanates for the preparation of a polyurethane polymer containing isocyanate groups are especially commercially available aliphatic, cycloaliphatic, arylaliphatic or aromatic, preferably cycloaliphatic or aromatic, diisocyanates.

Preferred diisocyanates are hexamethylene 1,6-diisocyanate (HDI), 1-isocyanato-3,3,5-trimethyl-5-isocyanatomethylcyclohexane (=isophorone diisocyanate or IPDI), tolylene 2,4- and/or 2,6-diisocyanate (TDI) or any desired mixtures of these isomers, diphenylmethane 4,4'-, 2,4'- and/or 2,2'-diisocyanate or any desired mixtures of these isomers (MDI).

For the reaction with polyols that are liquid at room temperature, IPDI or TDI is most preferred. In this way, polymers with low viscosity are obtained. Very particular preference is given to IPDI. In this way, particularly lightfast polymers are obtainable.

For the reaction with polyols that are solid at room temperature, IPDI or MDI is most preferred. In this way, especially polymers for reactive hotmelt adhesives having particularly advantageous properties are obtainable.

In the preparation of the polymer having end groups of the formula (I), in addition to the polyol, it is possible to use further alcohols, especially mono- or polyhydric alcohols of low molecular weight or polymeric monools. Such alcohols can be used as an addition to the polyol in the preparation of the polyurethane polymer containing isocyanate groups, or they can be added after the reaction of the hydroxysilane of the formula (III) and the polyurethane polymer containing isocyanate groups, for example in order to react with isocyanate groups present. It may especially be advantageous to admix a polymer having end groups of the formula (I) that additionally contains isocyanate groups with ethanol, for example, in order to convert the isocyanate groups. Subsequently, excess ethanol can be removed by distillation.

A hydroxysilane of the formula (III) suitable for reaction with the polyurethane polymer containing isocyanate groups is preferably obtained by the reaction of at least one epoxysilane of the formula (IV) with at least one alcohol or thiol or phenol or thiophenol of the formula (V).

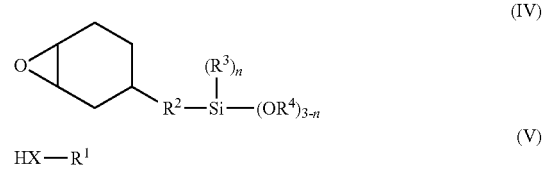

(IV)

HX—R¹  (V)

In the formulae (IV) and (V), $R^1$, $R^2$, $R^3$, $R^4$, X and n have the definitions already given above.

An alcohol or thiol or phenol or thiophenol of the formula (V) may be added on here at the carbon either in the 2 or 3 position to the carbon atom to which the substituent containing silane groups is bonded, giving rise either to a hydroxysilane of the formula (IIIa) or a hydroxysilane of the formula (IIIb). This reaction typically affords mixtures of the two hydroxysilanes of the formula (IIIa) and (IIIb).

The reaction is preferably conducted at temperatures in the range from 50 to 140° C., especially 70 to 120° C.

If an alcohol of the formula (V) is used, it is preferably chosen such that the $R^1$ radical is the same as the $R^4$ radical of the epoxysilane of the formula (IV). The alcohol of the formula (V) is preferably used in a stoichiometric or superstoichiometric ratio in relation to the epoxysilane of the formula (IV). More particularly, an alcohol/epoxysilane ratio in the range from 1.0 to 6.0, preferably 2.0 to 5.0, is employed.

If a thiol or a phenol or a thiophenol of the formula (V) is used, it is preferably used in a substoichiometric or stoichiometric ratio in relation to the epoxysilane of the formula (IV). More particularly, a thiol/epoxysilane or phenol/epoxysilane or thiophenol/epoxysilane ratio in the range from 0.5 to 1.0, preferably 0.8 to 1.0, is employed. Excess thiol or phenol or thiophenol can lead to odor or toxicological problems.

It is possible to use a catalyst in the reaction, especially an imidazole, a hydroxyalkylamine, an alcohol, a phenol, a Brønsted acid such as, more particularly, acetic acid or methanesulfonic acid, a Lewis acid such as, more particularly, aluminum(III) acetylacetonate, aluminum(III) isopropoxide, aluminum(III) ethoxide, lanthanum(III) triflate, zinc dichloride or zinc bis(ethylhexanoate), or a metal salt such as, more particularly, sodium dodecylsulfate or lithium perchlorate.

Preferably, after the reaction, any volatile compounds present, especially excess alcohol, are removed from the reaction product, especially by distillation.

If an alcohol in which the $R^1$ radical differs from the $R^4$ radical of the silane group is used, it is possible for transesterification reactions on the silane group to occur during the preparation, forming hydroxysilanes with alkoxy groups derived from the alcohol of the formula (V) used on the silicon.

In one embodiment of the preparation, preference is given to using that alcohol which corresponds to the alkoxy groups on the epoxysilane used. The hydroxysilane of the formula (III) is especially formed here in a purity of at least 80% by weight, preferably at least 85% by weight. The high purity of such hydroxysilanes is surprising, given that hydroxysilanes according to the prior art typically have contents of impurities of 20% by weight or more.

The epoxysilane of the formula (IV) used is preferably a β-(3,4-epoxycyclohexyl)ethyltrialkoxysilane. Particularly suitable examples are β-(3,4-epoxycyclohexyl)ethyltrimethoxysilane, commercially available, for example, as Silquest® A-186 (from Momentive Performance Materials), or β-(3,4-epoxycyclohexyl)ethyltriethoxysilane, commercially available, for example, as CoatOSil® 1770 (from Momentive Performance Materials).

Suitable alcohols of the formula (V) are aliphatic or cycloaliphatic or arylaliphatic alcohols, especially methanol, ethanol, 1-propanol, isopropanol, 1-butanol, 2-butanol, isobutanol, 1-pentanol (amyl alcohol), isopentanol (isoamyl alcohol), 2-methyl-1-butanol, 2-pentanol, 3-pentanol, 1-hexanol, 2-methyl-1-pentanol, 4-methyl-2-pentanol, 2-ethyl-1-butanol, 1-heptanol, 1-octanol, 2-ethyl-1-hexanol, 1-nonanol, 1-decanol, 1-undecanol, 1-dodecanol, 1-methoxy-2-propanol, 2-methoxyethanol (methylglycol), 2-(2-methoxyethoxy)ethanol (methyldiglycol), cyclohexanol, 2-methylcyclohexanol, 4-methylcyclohexanol, benzyl alcohol, 2-methylbenzyl alcohol, 4-methylbenzyl alcohol, 4-ethylbenzyl alcohol, 4-isopropylbenzyl alcohol, 4-tert-butylbenzyl alcohol, 4-methoxybenzyl alcohol, N,N-dimethylethanolamine, N,N-diethylethanolamine, N,N-dibutylethanolamine or N-(2-hydroxyethyl)morpholine.

Among these, preference is given to methanol, ethanol, isopropanol, 1-butanol, isobutanol, 1-pentanol, 1-hexanol, 2-methoxyethanol, 2-(2-methoxyethoxy)ethanol, cyclohexanol or benzyl alcohol.

Particular preference is given to methanol or ethanol.

Particularly advantageously, the alcohol of the formula (V) employed is methanol in the case of use of an epoxysilane having methoxysilane groups, and is ethanol in the case of use of an epoxysilane having ethoxysilane groups.

Suitable thiols of the formula (V) are aliphatic or cycloaliphatic or arylaliphatic thiols, especially 2-(2-methoxyethoxy)ethanethiol, methyl thioglycolate, ethyl thioglycolate, 2-ethylhexyl thioglycolate, methyl 3-mercaptopropionate, ethyl 3-mercaptopropionate or 2-ethylhexyl 3-mercaptopropionate. Among these, preference is given to 2-(2-methoxyethoxy)ethanethiol or 2-ethylhexyl thioglycolate.

Suitable phenols of the formula (V) are especially phenol, o-cresol, m-cresol, p-cresol, 4-tert-butylphenol, 4-nonylphenol, 4-dodecylphenol, 2,3-dimethylphenol (o-xylenol), 2,4-dimethylphenol (m-xylenol), 2,5-dimethylphenol (p-xylenol), 2,6-dimethylphenol, 3,4-dimethylphenol, 3,5-dimethylphenol, 2-methoxyphenol (guaiacol), 3-methoxyphenol, 4-methoxyphenol, 2,6-dimethoxyphenol, 2,4,6-tris(dimethylaminomethyl)phenol, 1-naphthol or 2-naphthol. Among these, preference is given to 4-tert-butylphenol, 4-nonylphenol, 4-dodecylphenol, o-xylenol, m-xylenol or p-xylenol.

Suitable thiophenols of the formula (V) are especially thiophenol, 4-methylthiophenol, 4-tert-butylthiophenol, 4-nonylthiophenol, 4-dodecylthiophenol, 2,5-dimethylthiophenol, 2,6-dimethylthiophenol, 3-methoxythiophenol, 4-methoxythiophenol, 1-thionaphthol or 2-thionaphthol.

Preferred alcohols or thiols or phenols or thiophenols of the formula (V) are alcohols.

The hydroxysilane of the formula (III) for reaction with the polyurethane polymer containing isocyanate groups is preferably selected from the group consisting of 2-methoxy-4-(2-trimethoxysilylethyl)cyclohexan-1-ol, 2-methoxy-4-(2-ethoxydimethoxysilylethyl)cyclohexan-1-ol, 2-methoxy-4-(2-methoxydiethoxysilylethyl)cyclohexan-1-ol, 2-methoxy-4-(2-triethoxysilylethyl)cyclohexan-1-ol, 2-ethoxy-4-(2-trimethoxysilylethyl)cyclohexan-1-ol, 2-ethoxy-4-(2-ethoxydimethoxysilylethyl)cyclohexan-1-ol, 2-ethoxy-4-(2-methoxydiethoxysilylethyl)cyclohexan-1-ol, 2-ethoxy-4-(2-triethoxysilylethyl)cyclohexan-1-ol, 2-isopropoxy-4-(2-triisopropoxysilylethyl)cyclohexan-1-ol, 2-isopropoxy-4-(2-methoxydiisopropoxysilylethyl)cyclohexan-1-ol, 2-isopropoxy-4-(2-ethoxydiisopropoxysilylethyl)cyclohexan-1-ol, 2-isopropoxy-4-(2-isopropoxydimethoxysilylethyl)cyclohexan-1-ol, 2-isopropoxy-4-(2-isopropoxydiethoxysilylethyl)cyclohexan-1-ol, 2-isopropoxy-4-(2-trimethoxysilylethyl)cyclohexan-1-ol, 2-isopropoxy-4-(2-triethoxysilylethyl)cyclohexan-1-ol, 2-butoxy-4-(2-tributoxysilylethyl)cyclohexan-1-ol, 2-butoxy-4-(2-methoxydibutoxysilylethyl)cyclohexan-1-ol, 2-butoxy-4-(2-ethoxydibutoxysilylethyl)cyclohexan-1-ol, 2-butoxy-4-(2-butoxydimethoxysilylethyl)cyclohexan-1-ol, 2-butoxy-4-(2-butoxydiethoxysilylethyl)cyclohexan-1-ol, 2-butoxy-4-(2-trimethoxysilylethyl)cyclohexan-1-ol, 2-butoxy-4-(2-triethoxysilylethyl)cyclohexan-1-ol, 2-isobutoxy-4-(2-triisobutoxysilylethyl)cyclohexan-1-ol, 2-isobutoxy-4-(2-methoxydiisobutoxysilylethyl)cyclohexan-1-ol, 2-isobutoxy-4-(2-ethoxydiisobutoxysilylethyl)cyclohexan-1-ol, 2-isobutoxy-4-(2-isobutoxydimethoxysilylethyl)cyclohexan-1-ol, 2-isobutoxy-4-(2-isobutoxydiethoxysilylethyl)cyclohexan-1-ol, 2-isobutoxy-4-(2-trimethoxysilylethyl)cyclohexan-1-ol, 2-isobutoxy-4-(2-triethoxysilylethyl)cyclohexan-1-ol, 2-pentoxy-4-(2-tripentoxysilylethyl)cyclohexan-1-ol, 2-pentoxy-4-(2-methoxydipentoxysilylethyl)cyclohexan-1-ol, 2-pentoxy-4-(2-ethoxydipentoxysilylethyl)cyclohexan-1-ol, 2-pentoxy-4-(2-pentoxydimethoxysilylethyl)cyclohexan-1-ol, 2-pentoxy-4-(2-pentoxydiethoxysilylethyl)cyclohexan-1-ol, 2-pentoxy-4-(2-trimethoxysilylethyl)cyclohexan-1-ol, 2-pentoxy-4-(2-triethoxysilylethyl)cyclohexan-1-ol, 2-hexoxy-4-(2-trihexoxysilylethyl)cyclohexan-1-ol, 2-hexoxy-4-(2-methoxydihexoxysilylethyl)cyclohexan-1-ol, 2-hexoxy-4-(2-ethoxydihexoxysilylethyl)cyclohexan-1-ol, 2-hexoxy-4-(2-hexoxydimethoxysilylethyl)cyclohexan-1-ol, 2-hexoxy-4-(2-hexoxydiethoxysilylethyl)cyclohexan- 1-ol, 2-hexoxy-4-(2-trimethoxysilylethyl)cyclohexan-1-ol, 2-hexoxy-4-(2-triethoxysilylethyl)cyclohexan-1-ol, 2-(2-methoxyethoxy)-4-(2-tris(2-methoxyethoxy)silylethyl)cyclohexan-1-ol, 2-(2-methoxyethoxy)-4-(2-methoxybis(2-methoxyethoxy)silylethyl)cyclohexan-1-ol, 2-(2-methoxyethoxy)-4-(2-ethoxybis(2-methoxyethoxy)silylethyl)cyclohexan-1-ol, 2-(2-methoxyethoxy)-4-(2-dimethoxy-(2-methoxyethoxy)silylethyl)cyclohexan-1-ol, 2-(2-methoxyethoxy)-4-(2-diethoxy-(2-methoxyethoxy)silylethyl)cyclohexan-1-ol, 2-(2-methoxyethoxy)-4-(2-trimethoxysilylethyl)cyclohexan-1-ol, 2-(2-methoxyethoxy)-4-(2-triethoxysilylethyl)cyclohexan-1-ol, 2-(2-methoxyethoxy)ethoxy-4-(2-tris(2-(2-methoxyethoxy)ethoxy)silylethyl)cyclohexan-1-ol, 2-(2-methoxyethoxy)ethoxy-4-(2-methoxybis(2-(2-methoxyethoxy)ethoxy)silylethyl)cyclohexan-1-ol, 2-(2-methoxyethoxy)ethoxy-4-(2-ethoxybis(2-(2-methoxyethoxy)ethoxy)silylethyl)cyclohexan-1-ol, 2-(2-methoxyethoxy)ethoxy-4-(2-dimethoxy-(2-(2-methoxyethoxy)ethoxy)silylethyl)cyclohexan-1-ol, 2-(2-methoxyethoxy)ethoxy-4-(2-diethoxy-(2-(2-methoxyethoxy)ethoxy)silylethyl)cyclohexan-1-ol, 2-(2-methoxyethoxy)ethoxy-4-(2-trimethoxysilylethyl)cyclohexan-1-ol, 2-(2-methoxyethoxy)ethoxy-4-(2-triethoxysilylethyl)cyclohexan-1-ol, 2-cyclohexoxy-4-(2-tricyclohexoxysilylethyl)cyclohexan-1-ol, 2-cyclohexoxy-4-(2-methoxydicyclohexoxysilylethyl)cyclohexan-1-ol, 2-cyclohexoxy-4-(2-ethoxydicyclohexoxysilylethyl)cyclohexan-1-ol, 2-cyclohexoxy-4-(2-cyclohexoxydimethoxysilylethyl)cyclohexan-1-ol, 2-cyclohexoxy-4-(2-cyclohexoxydiethoxysilylethyl)cyclohexan-1-ol, 2-cyclohexoxy-4-(2-trimethoxysilylethyl)cyclohexan-1-ol, 2-cyclohexoxy-4-(2-triethoxysilylethyl)cyclohexan-1-ol, 2-benzoxy-4-(2-tribenzoxysilylethyl)cyclohexan-1-ol, 2-benzoxy-4-(2-methoxydibenzoxysilylethyl)cyclohexan-1-ol, 2-benzoxy-4-(2-ethoxydibenzoxysilylethyl)cyclohexan-1-ol, 2-benzoxy-4-(2-benzoxydimethoxysilylethyl)cyclohexan-1-ol, 2-benzoxy-4-(2-benzoxydiethoxysilylethyl)cyclohexan-1-ol, 2-benzoxy-4-(2-trimethoxysilylethyl)cyclohexan-1-ol, 2-benzoxy-4-(2-triethoxysilylethyl)cyclohexan-1-ol, and the corresponding compounds in which the substituent containing silane groups is in the 5 position rather than in the 4 position.

Among these, preference is given to 2-methoxy-4-(2-trimethoxysilylethyl)cyclohexan-1-ol, 2-ethoxy-4-(2-triethoxysilylethyl)cyclohexan-1-ol, 2-ethoxy-4-(2-trimethoxysilylethyl)cyclohexan-1-ol, 2-ethoxy-4-(2-ethoxydimethoxysilylethyl)cyclohexan-1-ol, 2-ethoxy-4-(2-methoxydiethoxysilylethyl)cyclohexan-1-ol, 2-(2-methoxyethoxy)ethoxy-4-(2-tris(2-(2-methoxyethoxy)ethoxy)silylethyl)cyclohexan-1-ol, or the corresponding compounds in which the substituent containing silane groups is in the 5 position rather than in the 4 position.

Most preferred is 2-ethoxy-4(5)-(2-triethoxysilylethyl)cyclohexan-1-ol or 2-methoxy-4(5)-(2-trimethoxysilylethyl)cyclohexan-1-ol.

Mixtures of two compounds wherein the substituent containing silane groups is in the 4 or in the 5 position are represented by the notation "4(5)".

With the preferred hydroxysilanes, polymers having good storage stability are obtained, which cure rapidly with moisture to give crosslinked plastics having good thermal stability.

The invention further provides a hydroxysilane of the formula (VII)

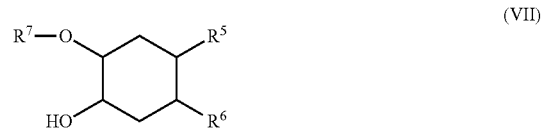

where
either $R^5$ is a radical of the formula (VIII) and $R^6$ is a hydrogen radical
or $R^5$ is a hydrogen radical and $R^6$ is a radical of the formula (VIII);

and $R^7$ and $R^8$ are either each a methyl radical or each an ethyl radical.

The hydroxysilane of the formula (VII) corresponds either to the formula (VIIa) or to the formula (VIIb)

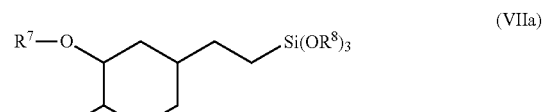

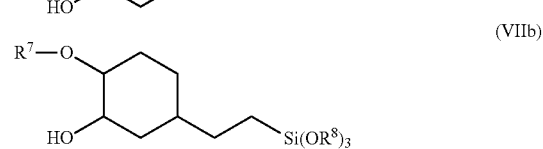

In the formulae (VIIa) and (VIIb), $R^7$ and $R^8$ have the definitions already given above.

The formulae (VIIa) and (VIIb) include all the diastereomers possible for the particular structure.

The hydroxysilane of the formula (VII) is preparable in a particularly simple manner and particularly pure quality and is particularly suitable for the preparation of a polymer having end groups of the formula (I).

The polymer having end groups of the formula (I) is storage-stable with exclusion of moisture. On contact with moisture, the end groups of the formula (I) are hydrolyzed. This forms silanol groups (Si—OH groups), and subsequent condensation reactions form siloxane groups (Si—O—Si groups). Any further moisture-reactive groups present, especially isocyanate groups, likewise react with moisture present. As a result of these reactions, the polymer cures to give a crosslinked plastic. The moisture for the curing can either come from the air (air humidity), or the polymer can be contacted with a water-containing component, for example by spreading, spraying or mixing-in. During the curing, silanol groups can condense, for example, with hydroxyl groups in a substrate to which the polymer has been applied, as a result of which an additional improvement in the adhesion on the substrate is possible in the course of crosslinking.

A hydrolyzed or partially hydrolyzed polymer having end groups of the formula (I) contains end groups having at least one silanol group of the formula (VI).

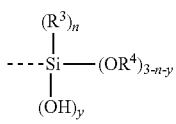

(VI)

In the formula (VI), y is 1 or 2 or 3, with the proviso that y has not more than the value of (3-n). $R^3$, $R^4$ and n have the definitions already given.

The polymer having end groups of the formula (I) has advantageous properties. It has a relatively low viscosity, which is advantageous for the further processing thereof, especially as a constituent of a curable composition. It is very storage-stable and, coupled with a long open time, cures surprisingly rapidly with moisture to give a cross-linked material having good adhesion properties.

A polymer having end groups of the formula (I) which is liquid at room temperature cures with moisture at room temperature to give an elastic nontacky material having high strength, high extensibility and good thermal stability. At high temperatures such as 90° C. or 100° C., the cured polymer remains elastic even after prolonged exposure, whereas many polymers containing silane groups from the prior art lose strength or even deliquesce after just a short time.

A polymer having end groups of the formula (I) which is solid at room temperature, in the uncrosslinked state, has good thermal stability, meaning that it can be left for a while in the heated molten state without occurrence of any significant increase in viscosity or gelation. It crosslinks with moisture to give a material of high bond strength, which cannot be melted again when reheated.

The present invention further provides a curable composition comprising at least one polymer having end groups of the formula (I), as previously described.

Preferably, the curable composition comprises at least one further constituent selected from fillers, crosslinkers, plasticizers, solvents, catalysts, adhesion promoters, desiccants, stabilizers, pigments and rheology aids.

Preferably, the curable composition is an adhesive or a sealant or a coating.

In a preferred embodiment, the curable composition is applicable at room temperature and is especially an elastic adhesive or sealant or an elastic coating, especially for joint sealing or for elastic adhesive bonds in construction or industrial applications. Typically, it comprises a polymer having end groups of the formula (I) which is liquid at room temperature.

A curable composition applicable at room temperature can be converted to the desired shape at room temperature before it cures. It is liquid and/or spreadable at room temperature.

Preferably, the composition applicable at room temperature has a content of polymer having end groups of the formula (I) of 5% to 90% by weight, especially 10% to 60% by weight.

Suitable further constituents are especially catalysts, crosslinkers, plasticizers, fillers, pigments, solvents, adhesion promoters, desiccants, rheology aids or stabilizers.

Preferably, the composition applicable at room temperature comprises at least one catalyst which accelerates the crosslinking of polymers containing silane groups. Especially suitable for the purpose are metal catalysts and/or nitrogen compounds.

Suitable metal catalysts are especially compounds of titanium, zirconium, aluminum or tin, especially organotin compounds, organotitanates, organozirconates or organoaluminates, where these compounds especially have alkoxy groups, aminoalkoxy groups, sulfonate groups, carboxyl groups, 1,3-diketonate groups, 1,3-ketoesterate groups, dialkylphosphate groups and dialkylpyrophosphate groups.

Particularly suitable organotin compounds are dialkyltin oxides, dialkyltin dichlorides, dialkyltin dicarboxylates and dialkyltin diketonates, especially dibutyltin oxide, dibutyltin dichloride, dibutyltin diacetate, dibutyltin dilaurate, dibutyltin diacetylacetonate, dioctyltin oxide, dioctyltin dichloride, dioctyltin diacetate, dioctyltin dilaurate and dioctyltin diacetylacetonate, or alkyltin thioesters.

Particularly suitable organotitanates are:
  titanium(IV) complexes having two 1,3-diketonate ligands, especially 2,4-pentanedionate (=acetylacetonate), and two alkoxide ligands;
  titanium(IV) complexes having two 1,3-ketoesterate ligands, especially ethylacetoacetate, and two alkoxide ligands;
  titanium(IV) complexes having one or more aminoalkoxide ligands, especially triethanolamine or 2-((2-aminoethyl)amino)ethanol, and one or more alkoxide ligands;
  titanium(IV) complexes having four alkoxide ligands;
  or more highly condensed organotitanates, especially oligomeric titanium(IV) tetrabutoxide, also referred to as polybutyl titanate;
where suitable alkoxide ligands are especially isobutoxy, n-butoxy, isopropoxy, ethoxy and 2-ethylhexoxy.

Very particularly suitable organotitanates are bis(ethylacetoacetato)diisobutoxytitanium(IV), bis(ethylacetoacetato)diisopropoxytitanium(IV), bis(acetylacetonato)diisopropoxytitanium(IV), bis(acetylacetonato)diisobutoxytitanium(IV), tris(oxyethyl)amineisopropoxytitanium(IV), bis[tris(oxyethyl)amine]diisopropoxytitanium(IV), bis(2-ethylhexane-1,3-dioxy)titanium(IV), tris[2-((2-aminoethyl)amino)ethoxy]ethoxytitanium(IV), bis(neopentyl(diallyl)oxydiethoxytitanium(IV), titanium(IV) tetrabutoxide, tetra(2-ethylhexyloxy)titanate, tetra(isopropoxy)titanate or polybutyl titanate. Especially suitable are the following commercially available products: Tyzor® AA, GBA, GBO, AA-75, AA-65, AA-105, DC, BEAT, BTP, TE, TnBT, KTM, TOT, TPT or IBAY (all from Dorf Ketal); Tytan PBT, TET, X85, TAA, ET, S2, S4 or S6 (all from Borica Company Ltd.) and Ken-React® KR® TTS, 7, 9QS, 12, 26S, 33DS, 38S, 39DS, 44, 134S, 138S, 133DS, 158FS or LICA® 44 (all from Kenrich Petrochemicals).

Particularly suitable organozirconates are the following commercially available products: Ken-React® NZ® 38J, KZ® TPPJ, KZ® TPP, NZ® 01, 09, 12 38, 44 or 97 (all from Kenrich Petrochemicals) or Snapcure® 3020, 3030, 1020 (all from Johnson Matthey & Brandenberger).

A particularly suitable organoaluminate is the commercially available product K-Kat 5218 (from King Industries).

Nitrogen compounds suitable as catalyst are especially amines such as, more particularly, N-ethyldiisopropylamine, N,N,N',N'-tetramethylalkylenediamines, polyoxyalkyleneamines, 1,4-diazabicyclo[2.2.2]octane; aminosilanes such as, more particularly, 3-aminopropyltrimethoxysilane, 3-aminopropyldimethoxymethylsilane, N-(2-aminoethyl)-3-aminopropyltrimethoxysilane, N-(2-aminoethyl)-3-aminopropylmethyldimethoxysilane, N-(2-aminoethyl)-N'-[3-(trimethoxysilyl)-propyl]ethylenediamine or the analogs thereof having ethoxy or isopropoxy in place of the methoxy groups on the silicon; cyclic amidines such as, more particularly, 1,8-diazabicyclo[5.4.0]undec-7-ene (DBU), 1,5-diazabicyclo[4.3.0]non-5-ene (DBN), 6-dibutylamino-1,8-diazabicyclo[5.4.0]undec-7-ene; guanidines such as, more particularly, tetramethylguanidine, 2-guanidinobenzimidazole, acetylacetoneguanidine, 1,3-di-o-tolylguanidine, 2-tert-butyl-1,1,3,3-tetramethylguanidine; or reaction products of carbodiimides and amines, such as, more particularly, polyetheramines or aminosilanes; oder imidazoles such as, more particularly, N-(3-trimethoxysilylpropyl)-4,5-dihydroimidazole and N-(3-triethoxysilylpropyl)-4,5-dihydroimidazole.

Also suitable are combinations of various catalysts, especially combinations of at least one metal catalyst and at least one nitrogen compound.

Preferred catalysts are organotin compounds, organotitanates, amines, amidines, guanidines and imidazoles.

Particular preference is given to organotitanates and amidines.

Further suitable constituents of the composition applicable at room temperature are especially the following auxiliaries and additives:

adhesion promoters and/or crosslinkers, especially silanes such as, more particularly, aminosilanes such as, more particularly, 3-aminopropyltrimethoxysilane, 3-aminopropyldimethoxymethylsilane, N-(2-aminoethyl)-3-aminopropyltrimethoxysilane, N-(2-aminoethyl)-3-aminopropylmethyldimethoxysilane, N-(2-aminoethyl)-N'-[3-(trimethoxysilyl)-propyl] ethylenediamine and the analogs thereof having ethoxy or isopropoxy in place of the methoxy groups on the silicon, N-phenyl-, N-cyclohexyl- or N-alkylaminosilanes, and also mercaptosilanes, epoxysilanes, (meth) acryloylsilanes, anhydridosilanes, carbamatosilanes, alkylsilanes or iminosilanes, or oligomeric forms of these silanes, or adducts formed from primary aminosilanes with epoxysilanes or (meth)acryloylsilanes or anhydridosilanes. Especially suitable are 3-glycidoxypropyltrimethoxysilane, 3-aminopropyltrimethoxysilane, N-(2-aminoethyl)-3-aminopropyltrimethoxysilane, N-(2-aminoethyl)-N'-[3-(trimethoxysilyl)propyl] ethylenediamine, 3-mercaptopropyltrimethoxysilane, 3-ureidopropyltrimethoxysilane and the corresponding silanes having ethoxy groups in place of the methoxy groups, or oligomeric forms of these silanes.

plasticizers, especially carboxylic esters such as phthalates, especially dioctyl phthalate, diisononyl phthalate or diisodecyl phthalate, adipates, especially dioctyl adipate, azelates, sebacates, polyols, especially polyoxyalkylenepolyols or polyesterpolyols, glycol ethers, glycol esters, organic phosphoric or sulfonic esters, polybutenes, or fatty acid methyl or ethyl esters derived from natural fats or oils, also called "biodiesel";

solvents;

inorganic and organic fillers, especially natural, ground or precipitated calcium carbonates optionally coated with fatty acids, especially stearic acid, baryte (heavy spar), talcs, quartz flours, quartz sand, dolomites, wollastonites, kaolins, calcined kaolins, mica, molecular sieves, aluminum oxides, aluminum hydroxides, magnesium hydroxide, silicas including finely divided silicas from pyrolysis processes, industrially produced carbon blacks, graphite, metal powders such as aluminum, copper, iron, silver or steel, PVC powder or hollow beads;

fibers, especially glass fibers, carbon fibers, metal fibers, ceramic fibers or polymer fibers such as polyamide fibers or polyethylene fibers;

dyes;

pigments, especially titanium dioxide or iron oxides;

desiccants, especially tetraethoxysilane, vinyltrimethoxy- or vinyltriethoxysilane and organoalkoxysilanes having a functional group in the α position to the silane group, especially N-(methyldimethoxysilylmethyl)-O-methyl-carbamate, (methacryloyloxymethyl)silanes, methoxymethylsilanes, orthoformic esters, or calcium oxide or molecular sieves;

rheology modifiers, especially thickeners, especially sheet silicates such as bentonites, derivatives of castor oil, hydrogenated castor oil, polyamides, polyurethanes, urea compounds, fumed silicas, cellulose ethers or hydrophobically modified polyoxyethylenes;

stabilizers against oxidation, heat, light or UV radiation;

natural resins, fats or oils such as rosin, shellac, linseed oil, castor oil or soya oil;

nonreactive polymers such as, more particularly, homo- or copolymers of unsaturated monomers, especially from the group comprising ethylene, propylene, butylene, isobutylene, isoprene, vinyl acetate and alkyl (meth) acrylates, especially polyethylenes (PE), polypropylenes (PP), polyisobutylenes, ethylene-vinyl acetate copolymers (EVA) or atactic poly-α-olefins (APAO);

flame-retardant substances, especially the aluminum hydroxide and magnesium hydroxide fillers already mentioned, and also especially organic phosphoric esters such as, more particularly, triethyl phosphate, tricresyl phosphate, triphenyl phosphate, diphenyl cresyl phosphate, isodecyl diphenyl phosphate, tris(1,3-dichloro-2-propyl) phosphate, tris(2-chloroethyl) phosphate, tris(2-ethylhexyl) phosphate, tris(chloroisopropyl) phosphate, tris(chloropropyl) phosphate, isopropylated triphenyl phosphate, mono-, bis- and tris(isopropylphenyl) phosphate of different isopropylation levels, resorcinolbis(diphenyl phosphate), bisphenol A bis(diphenyl phosphate) or ammonium polyphosphates;

surface-active substances, especially wetting agents, leveling agents, deaerators or defoamers;

biocides, especially algicides, fungicides or substances that inhibit fungal growth;

or further substances customarily used in moisture-curing compositions.

It may be advisable to chemically or physically dry certain constituents before mixing them into the composition.

The composition applicable at room temperature may, as well as the polymer having end groups of the formula (I), comprise further oligo- or polymers containing silane groups.

In a preferred embodiment, it is free of organotin compounds. This may be advantageous for environmental and/or toxicological reasons.

In a preferred embodiment, it does not release any methanol in the course of curing. This may be advantageous for toxicological reasons.

The composition applicable at room temperature is preferably produced and stored with exclusion of moisture. Typically, the composition is storage-stable with exclusion of moisture in a suitable package or arrangement, such as, more particularly, a drum, a pouch or a cartridge.

The composition applicable at room temperature may take the form of a one-component composition or of a two-component composition.

A "one-component" composition in the present document refers to a composition in which all the constituents of the composition are stored in a mixture in the same container and which is curable with moisture.

A "two-component" composition in the present document refers to a composition in which the constituents of the composition are present in two different components which are stored in separate containers. Only shortly before or during the application of the composition are the two components mixed with one another, and then the mixed composition cures, with the curing only proceeding or being completed through the action of moisture.

On application of the composition applicable at room temperature to at least one solid body or article, the silane groups present and any further moisture-reactive groups present come into contact with moisture, which results in curing of the composition. The curing proceeds at different speeds according to the temperature, the nature of the contact, the amount of moisture and the presence of any catalysts. In the case of curing by means of air humidity, a skin is at first formed on the surface of the composition. What is called the skin time is a measure of the curing rate.

The composition applicable at room temperature, in the cured state, especially has markedly elastic properties, especially high strength and high extensibility, good thermal stability and good adhesion properties on various substrates. As a result, it is suitable for a multitude of uses, especially as a sealant, adhesive, covering, coating or paint for construction or industrial applications, for example as a joint sealant, weld or flange seam sealant, parquet adhesive, assembly adhesive, bodywork adhesive, glazing adhesive, floor covering, floor coating, balcony coating, roof coating, or parking garage coating.

For use as an adhesive or sealant, the composition applicable at room temperature preferably has a pasty consistency with structurally viscous properties. Such a pasty sealant and/or adhesive is especially applied to a substrate from commercial cartridges which are operated manually or by means of compressed air, or from a drum or vat by means of a conveying pump or an extruder, optionally by means of an application robot.

Suitable substrates for bonding or sealing or coating are especially
- glass, glass ceramic, screen-printed ceramic, concrete, mortar, brick, tile, gypsum or natural stone such as granite or marble;
- metals and alloys such as aluminum, iron, steel and nonferrous metals, or surface-finished metals and alloys such as galvanized or chromed metals;
- leather, textiles, paper, wood, wood-based materials bonded with resins, for example phenolic, melamine or epoxy resins, resin-textile composites or further polymer composites;
- plastics, especially rigid or flexible PVC, ABS, polycarbonate (PC), polyamide (PA), polyester, PMMA, epoxy resins, PUR, POM, PO, PE, PP, EPM or EPDM, optionally with surface treatment of the plastics by means of plasma, corona or flames;
- fiber-reinforced plastics, such as carbon fiber-reinforced plastics (CFP), glass fiber-reinforced plastics (GFP) or sheet molding compounds (SMC);
- coated substrates, such as powder-coated metals or alloys;
- paints or lacquers, especially automotive topcoats.

The substrates may be pretreated if required prior to the application of the composition, especially by physical and/or chemical cleaning methods or the application of an adhesion promoter, an adhesion promoter solution or a primer.

It is possible for two identical or two different substrates to be bonded or sealed.

After the bonding or sealing of two substrates, a bonded or sealed article is obtained. Such an article may be a built structure, especially a built structure in construction or civil engineering, or it may be an industrial good or a consumer good, especially a window, a domestic appliance, or a means of transport such as, more particularly, an automobile, a bus, a truck, a rail vehicle, a ship, an aircraft or a helicopter, or an installable component thereof.

The composition applicable at room temperature has good storage stability and processibility and crosslinks with moisture to give a nontacky elastic material having good thermal stability.

In a preferred embodiment, the curable composition is applicable at room temperature and is especially an elastic adhesive or sealant or an elastic coating, especially for joint sealing or for elastic adhesive bonds in construction or industrial applications.

In a further preferred embodiment, the curable composition is solid at room temperature and is a hotmelt adhesive. Typically, it comprises a polymer having end groups of the formula (I) which is solid at room temperature.

Suitable further constituents for a hotmelt adhesive are especially the following auxiliaries and additives:
- further crosslinkable polymers, especially polymers having silane groups and/or having isocyanate groups;
- nonreactive thermoplastic polymers, especially homo- or copolymers of unsaturated monomers, especially from the group comprising ethylene, propylene, butylene, isobutylene, isoprene, vinyl acetate, and alkyl (meth) acrylate, especially polyethylene (PE), polypropylene (PP), polyisobutylene, ethylene-vinyl acetate copolymers (EVA) or atactic poly-α-olefins (APAO); and also polyesters, polyacrylates, polymethacrylates, polyacrylamides, polyacrylonitriles, polyimides, polyamides, polyvinyl chlorides, polysiloxanes, polyurethanes, polystyrenes, or combinations thereof, especially polyetheramide copolymers, styrene-butadiene-styrene copolymers, styrene-isoprene-styrene copolymers, styrene-ethylene-butylene-styrene copolymers, styrene-ethylene-propylene-styrene copolymers; butyl rubber, polyisobutylene or combinations thereof, asphalt, bitumen, crude rubber, fluorinated rubber or cellulose resins;
- tackifier resins, especially a hydrocarbon resin such as, more particularly, coumarone-indene resins, terpene resins, phenol-modified terpene resins, natural, optionally modified resins such as, more particularly, rosin, tung resin or tall oil resin, and also α-methylstyrene resins or polymeric lactic acid;
- plasticizers, especially carboxylic esters such as phthalates or adipates, polyols, organic phosphoric or sulfonic esters, or polybutenes;
- catalysts for the crosslinking reactions, especially metal catalysts and/or nitrogen-containing compounds, more particularly organotin compounds, organotitanates, amines, amidines, guanidines or imidazoles;
- stabilizers to counter oxidation, heat, hydrolysis, light, and UV radiation, biocides, fungicides or flame retardants;
- desiccants, especially tetraethoxysilane, vinyltrimethoxy- or vinyltriethoxysilane and organoalkoxysilanes having a functional group in the α position to the silane group, especially N-(methyldimethoxysilylmethyl)-O-methyl-carbamate, (methacryloyloxymethyl)silanes, methoxymethylsilanes, orthoformic esters, or calcium oxide or molecular sieves;

adhesion promoters and/or crosslinkers, especially silanes such as aminosilanes, mercaptosilanes, epoxysilanes, (meth)acryloylsilanes, anhydridosilanes, carbamatosilanes, alkylsilanes or iminosilanes;

inorganic and organic fillers, especially mineral fillers, molecular sieves, silicas including finely divided silicas from pyrolysis processes, industrially manufactured carbon blacks, graphite, metal powders, PVC powders or hollow beads;

dyes;

or further substances customarily used in reactive hotmelt adhesives. It may be advisable to chemically or physically dry certain constituents prior to the addition.

The hotmelt adhesive preferably has a content of polymer having end groups of the formula (I) which is solid at room temperature in the range from 5% to 100% by weight, especially 15% to 95% by weight, more preferably 30% to 90% by weight, most preferably 50% to 80% by weight.

The hotmelt adhesive preferably comprises at least one further polymer selected from the group consisting of thermoplastic polymers having isocyanate groups, nonreactive thermoplastic polymers and tackifier resins.

The hotmelt adhesive preferably has a content of polymers including the polymer having end groups of the formula (I) which is solid at room temperature in the range from 70% to 100% by weight, more preferably 80% to 100% by weight, especially 90% to 100% by weight.

In a preferred embodiment, the hotmelt adhesive is free of organotin compounds. This may be advantageous for environmental and/or toxicological reasons.

The hotmelt adhesive is storage-stable with exclusion of moisture in a suitable package or arrangement.

In the reaction with moisture, the silane groups are hydrolyzed, which ultimately leads to crosslinking of the adhesive. If the hotmelt adhesive, in addition to the silane groups, also contains isocyanate groups, these likewise react with moisture, which additionally contributes to crosslinking of the adhesive.

The hotmelt adhesive, when applied in the liquid state, is applied to at least one substrate. For this purpose, the hotmelt adhesive is heated beforehand at least to such an extent that it is in liquid form. Application is typically effected at a temperature within the range from 80 to 200° C., especially 100 to 180° C. During the processing, the uncrosslinked adhesive has good thermal stability. This is shown by the fact that the adhesive can be left in the hot liquid state over a period sufficient for proper application, especially for up to several hours, without any undue rise in its viscosity, especially without any gelation, and without occurrence of odor emissions.

The hotmelt adhesive applied is advantageously joined to a second substrate to give a bond before it has unduly solidified as a result of cooling.

The solidification of the adhesive as a result of cooling brings about a very rapid buildup of strength and a high initial strength of the bond. In addition to this physical curing of the adhesive, even after the solidification, crosslinking occurs in the adhesive via silane groups and any isocyanate groups as a result of moisture, as described above. This chemical crosslinking ultimately leads to a cured crosslinked adhesive which cannot be melted again by reheating to the application temperature.

Suitable substrates which can be bonded with the hotmelt adhesive are especially the substrates already mentioned. Preferred substrates are plastics, textiles, leather, wood, wood-based materials, polymer composites, paper, metals, paints or lacquers.

The substrates may have been pretreated prior to the application of the adhesive, for example by a physical and/or chemical cleaning operation or by the application of an adhesion promoter, an adhesion promoter solution or a primer.

It is possible for two identical or two different substrates to be bonded. The adhesive is either applied to one of the two substrates and joined to the other to give a bond, or it can be applied to both substrates to be bonded. Preference is given to the bonding of two different substrates.

The hotmelt adhesive can especially be used for construction and industrial applications, especially as laminating adhesive, laminate adhesive, packaging adhesive, textile adhesive or wood adhesive. It is particularly suitable for bonds in which the bonding site is visible, especially for the bonding of glass, for example in motor vehicle and window construction, and for the bonding of transparent packaging.

The use of the hotmelt adhesive results in an article. Preferred articles are automobile interior trim parts such as, more particularly, roof linings, sunscreens, dashboards, door side parts, rear shelves and the like, wood fiber materials from the shower and bathroom sector, decorative furniture films, membrane films comprising textiles such as, more particularly, cotton, polyester films in the apparel sector, composites made from textiles and foams for automotive finishing, or transparent packaging.

The hotmelt adhesive described has a number of advantages. It permits a low risk classification, since it has a low or even zero content of monomeric diisocyanates. It is storage-stable in a suitable package. When heated to a temperature in the range from 80 to 200° C., especially 100 to 180° C., it has a viscosity with which it has good applicability. It can be kept in the liquid hot state over a surprisingly long period without gelating. The adhesive crosslinks under the influence of moisture, does not form any bubbles in the process, and leads to a visually and mechanically high-quality adhesive bond with excellent adhesion and good stability to environmental influences.

EXAMPLES

Detailed hereinafter are working examples which are intended to illustrate the invention described in detail. It will be appreciated that the invention is not restricted to these described working examples.

"Standard climatic conditions" are understood to mean a temperature of 23±1° C. and a relative air humidity of 50±5%. "SCC" stands for standard climatic conditions.

"TFT" stands for "tack-free time".

$^1$H NMR spectra were measured in $CDCl_3$ on a Bruker Ascend 400 spectrometer at 400.14 MHz; the chemical shifts δ are reported in ppm relative to tetramethylsilane (TMS); the coupling constants J are reported in Hz.

Infrared spectra (FT-IR) were measured as undiluted films on a Nicolet iS5 FT-IR system, equipped with a horizontal ATR measurement unit with a diamond crystal, from Thermo Scientific; the absorption bands are reported in wavenumbers ($cm^{-1}$) (measurement window: 4000-650 $cm^{-1}$).

Gas chromatograms (GC) were measured in the temperature range from 60 to 320° C. with a heating rate of 15° C./min and a dwell time of 10 min at 320° C. The injector temperature was 250° C. A Zebron ZB-5 column was used (L=30 m, ID=0.25 mm, dj=0.5 μm) with a gas flow rate of 1.5 mL/min. Detection was effected by means of flame ionization (FID), with evaluation of the signals via the area percent method.

Viscosities were determined on a Rheotec RC30 thermostatted cone-plate viscometer (cone diameter 50 mm, cone angle 1°, cone tip-plate distance 0.05 mm, shear rate 10 s$^{-1}$) at 20° C.

1. Starting Materials Used and Abbreviations Therefor:

Acclaim® 12200 polyoxypropylenediol with a low level of unsaturation, OH number 11.0 mg KOH/g, water content about 0.02% by weight (from Bayer)
IPDI isophorone diisocyanate, Vestanat® IPDI (from Evonik Industries)
DIDP diisodecyl phthalate
VTEO vinyltriethoxysilane
VTMO vinyltrimethoxysilane
PCC precipitated calcium carbonate, Socal® U1 S2 (from Solvay)
GCC ground calcium carbonate, Omyacarb® 5 GU (from Omya)
IBAY bis(ethylacetoacetato)diisobutoxytitanium(IV), Tyzor® IBAY (from Dorf Ketal)
DBU 1,8-diazabicyclo[5.4.0]undec-7-ene
NCO polymer 1:

With exclusion of moisture, 720.0 g of Acclaim® 12200, 34.5 g of IPDI, 80.0 g of DIDP and 0.1 g of bismuth tris(neodecanoate) (10% by weight in DIDP) were heated to 90° C. while stirring constantly and left at this temperature until the content of free isocyanate groups, determined by titrimetry, had reached a stable value of 0.73% by weight. The isocyanate-functional polymer was cooled down to room temperature and stored with exclusion of moisture. It was clear and, the day after the preparation, had a viscosity of 31 Pa·s (20° C.).

Hydroxysilane 1: 2-Ethoxy-4(5)-(2-triethoxysilylethyl)cyclohexan-1-ol

In a round-bottom flask, 150.00 g of ethanol and 0.50 g of vinyltriethoxysilane were stirred under a nitrogen atmosphere at 50° C. for 15 min. Subsequently, 180.00 g (624 mmol) of β-(3,4-epoxycyclohexyl)ethyltriethoxysilane (CoatOSil® 1770, from Momentive) and 3.06 g of aluminum(III) isopropoxide were added, and the mixture was stirred at reflux at 100° C. under a nitrogen atmosphere for 16 h. Then the cloudy reaction mixture was cooled down to room temperature and filtered, and excess ethanol was evaporated on a rotary evaporator at 80° C. and 10 mbar. A colorless liquid product was obtained.

After the preparation, the product had a purity of 92% by weight (determined by means of gas chromatography). After storage with exclusion of moisture at room temperature for 3 months, the purity was unchanged.

FT-IR: 3444 (O—H), 2973, 2925, 2882, 2735, 1483, 1443, 1389, 1347, 1294, 1263, 1212, 1165, 1100, 1073, 1012, 953, 885, 860, 767, 710, 677.

$^1$H NMR: δ 3.81 (m, 6H, Si—O—CH$_2$—CH$_3$), 3.68 and 3.56 (2×m, 2×0.5H, (OH)C$^{cycl}$H), 3.64 and 3.43 (2×m, 2×1H, C$^{cycl}$H—O—CH$_2$—CH$_3$), 3.27 and 3.13 (2×m, 2×0.5H, C$^{cycl}$H—O—CH$_2$—CH$_3$), 2.50 (m, 1H, C$^{cycl}$H), 1.80, 1.64 and 1.48 (3×m, 6H, C$^{cycl}$H$_2$), 1.41 (m, 2H, C$^{cycl}$H—CH$_2$—CH$_2$—Si), 1.22 (m, 12H, Si—O—CH$_2$—CH$_3$), 0.61 (m, 2H, C$^{cycl}$H—CH$_2$—CH$_2$—Si).

GC: Four peaks at retention times from 12.57 min to 12.82 min with a total of 92 area % were detected, which were assigned to the diastereomers of 2-ethoxy-4-(2-triethoxysilylethyl)cyclohexan-1-ol and 2-ethoxy-5-(2-triethoxysilylethyl)cyclohexan-1-ol and were added up for the purity.

Hydroxysilane 2: 2-Methoxy-4(5)-(2-trimethoxysilylethyl)cyclohexan-1-ol

In a round-bottom flask, 104.35 g of methanol and 0.39 g of vinyltrimethoxysilane were stirred under a nitrogen atmosphere at 50° C. for 15 min. Then 153.74 g (624 mmol) of β-(3,4-epoxycyclohexyl)ethyltrimethoxysilane (Silquest® A-186, from Momentive) and 3.06 g of aluminum(III) isopropoxide were added and the cloudy mixture was reacted in 60 g portions in the microwave reactor, in each case at 140° C. and a pressure of about 12 bar for 30 min. Subsequently, the combined cloudy reaction mixtures were cooled down to room temperature and filtered, and excess methanol was evaporated on a rotary evaporator at 80° C. and 10 mbar.

A colorless liquid product was obtained.

After the preparation, the product had a purity of 91% by weight (determined by means of gas chromatography). After storage with exclusion of moisture at room temperature for 3 months, the purity was unchanged.

FT-IR: 3456 (O—H), 2924, 2839, 1454, 1411, 1381, 1349, 1292, 1270, 1190, 1157, 1077, 997, 935, 908, 889, 874, 776, 710, 675.

$^1$H NMR: δ 3.73 and 3.61 (2×m, 2×0.5H, (OH) C$^{cycl}$H), 3.57 (d, 9H, Si—O—CH$_3$), 3.37 (d, 3H, C$^{cycl}$H—O—CH$_3$), 3.20 and 3.07 (2×m, 2×0.5H, C$^{cycl}$H—O—CH$_3$), 2.60 (m, 1H, C$^{cycl}$H), 1.82, 1.72, 1.63 and 1.46 (4×m, 6H, C$^{cycl}$H$_2$), 1.39 (q, 2H, C$^{cycl}$H—CH$_2$—CH$_2$—Si), 0.62 (m, 2H, C$^{cycl}$H—CH$_2$—CH$_2$—Si).

GC: Two peaks at retention times from 11.57 min to 11.68 min with a total of 91 area % were detected, which were assigned to the diastereomers of 2-methoxy-4-(2-trimethoxysilylethyl)cyclohexan-1-ol and 2-methoxy-5-(2-trimethoxysilylethyl)cyclohexan-1-ol and were added up for the purity.

Hydroxysilane 3: Mixture Comprising 2-(2-methoxyethoxy)ethoxy-4(5)-(2-tris(2-(2-methoxyethoxy)ethoxy)silylethyl)cyclohexan-1-ol, 2-(2-methoxyethoxy)ethoxy-4(5)-(2-ethoxybis(2-(2-methoxyethoxy)ethoxy)silylethyl)cyclohexan-1-ol and 2-(2-methoxyethoxy)ethoxy-4(5)-(2-diethoxy-(2-(2-methoxyethoxy)ethoxy)silylethyl)cyclohexan-1-ol In a round-bottom flask, 117.04 g of methyldiglycol (2-(2-methoxyethoxy)ethanol), 50.00 g (203 mmol) of β-(3,4-epoxycyclohexyl)ethyltrimethoxysilane (Silquest® A-186, from Momentive) and 0.50 g of aluminum(III) isopropoxide were stirred under a nitrogen atmosphere at 120° C. for 1 h. Subsequently, at constant temperature, a clear distillate was collected via an uncooled distillation attachment at 400 mbar over 2 h, at 300 mbar over a further 2 h and at 150 mbar over a further 3 h, which was identified as almost pure methanol with traces of methyldiglycol by FT-IR. The reaction mixture was stirred at 140° C. and 50 mbar for 24 hours, until it was no longer possible to collect any more distillate. Finally, the excess methyldiglycol was removed at 120° C. and 0.5 mbar. A colorless liquid product was obtained.

FT-IR: 3473 (O—H), 2923, 2874, 2820, 1454, 1411, 1354, 1329, 1292, 1248, 1198, 1086, 1028, 958, 847, 770, 715, 681.

2. Polymers Containing Silane Groups:
Polymer STP-1:

With exclusion of moisture, 100.00 g of NCO polymer 1, 0.06 g of bismuth tris(neodecanoate) (10% by weight in DIDP) and 6.72 g of hydroxysilane 1 were stirred under a nitrogen atmosphere at 80° C. until no isocyanate groups were detectable any longer by means of IR spectroscopy (about 2 hours). The polymer containing silane groups was cooled down to room temperature and stored with exclusion of moisture. It was clear and, the day after the preparation, had a viscosity of 116 Pa·s (20° C.).

Polymer STP-2:

With exclusion of moisture, 100.00 g of NCO polymer 1, 0.06 g of bismuth tris(neodecanoate) (10% by weight in DIDP) and 5.58 g of hydroxysilane 2 were stirred under a nitrogen atmosphere at 80° C. until no isocyanate groups were detectable any longer by means of IR spectroscopy (about 2 hours). The polymer containing silane groups was cooled down to room temperature and stored with exclusion of moisture. It was clear and, the day after the preparation, had a viscosity of 91 Pa·s (20° C.).

Polymer STP-3:

With exclusion of moisture, 100.00 g of NCO polymer 1, 0.06 g of bismuth tris(neodecanoate) (10% by weight in DIDP) and 12.66 g of hydroxysilane 3 were stirred under a nitrogen atmosphere at 80° C. until no isocyanate groups were detectable any longer by means of IR spectroscopy (about 2 hours). The polymer containing silane groups was cooled down to room temperature and stored with exclusion of moisture. It was clear and, the day after the preparation, had a viscosity of 126 Pa·s (20° C.).

The polymers STP-1 to STP-3 are inventive polymers having end groups of the formula (I).

3. Moisture-Curing Compositions Applicable at Room Temperature:

Compositions Z1 to Z6:

For each composition, the ingredients as specified in table 1 were mixed in the amounts specified (in parts by weight) by means of a centrifugal mixer (SpeedMixer™ DAC 150, FlackTek Inc.) with exclusion of moisture, and stored. Each composition was tested as follows:

To determine the storage stability, the viscosity of the composition was determined "fresh" (on the day after the preparation) and "stored" (7 days in a closed container in an air circulation oven at 60° C.).

To determine the tack-free time (TFT), a few grams of the composition were applied to cardboard in a layer thickness of about 2 mm and, under standard climatic conditions, the time until, when the surface of the composition was tapped gently by means of an LDPE pipette, there were for the first time no remaining residues on the pipette was determined.

Shore A hardness was determined in accordance with DIN 53505 on test specimens which had been cured under standard climatic conditions for 14 days.

To determine the mechanical properties, the composition was cast on a PTFE-coated film to give a film of thickness 2 mm, which was stored under standard climatic conditions for 2 weeks, and some dumbbells having a length of 75 mm with a bar length of 30 mm and a bar width of 4 mm were punched out of the film and these were tested in accordance with DIN EN 53504 at a pulling speed of 200 mm/min for tensile strength (breaking force), elongation at break and modulus of elasticity (modulus of elasticity at 0.5%-5% elongation).

These results are appended with "SCC:".

As a measure of thermal stability, some dumbbells and the Shore A test specimen after the 2 weeks under standard climatic conditions were additionally stored in an air circulation oven at 100° C. for 4 weeks and then tested in the same way for tensile strength, elongation at break and modulus of elasticity, or for Shore A hardness. These results are appended with "100° C.:". The results are reported in table 1.

The thickener paste was produced by initially charging a vacuum mixer with 300 g of diisodecyl phthalate and 48 g of 4,4'-methylene diphenyl diisocyanate (Desmodur® 44 MC L; from Bayer), heating them gently and then, while stirring vigorously, gradually adding 27 g of monobutylamine dropwise. The resultant paste was stirred for a further hour under vacuum and while cooling.

TABLE 1

| Composition and properties of the compositions Z1 to Z6. | | | | | | |
|---|---|---|---|---|---|---|
| Composition | Z1 | Z2 | Z3 | Z4 | Z5 | Z6 |
| Polymer containing silane groups | STP-1, 20.0 | STP-1, 20.0 | STP-2, 20.0 | STP-2, 20.0 | STP-3, 20.0 | STP-3, 20.0 |
| DIDP | 17.6 | 17.6 | 17.6 | 17.6 | 17.6 | 17.6 |
| Thickener paste | 5.9 | 5.9 | 5.9 | 5.9 | 5.9 | 5.9 |
| VTEO | 1.0 | 1.0 | — | — | 1.0 | 1.0 |
| VTMO | — | — | 1.0 | 1.0 | — | — |
| PCC | 10.0 | 10.0 | 10.0 | 10.0 | 10.0 | 10.0 |
| GCC | 50.0 | 50.0 | 50.0 | 50.0 | 50.0 | 50.0 |
| IBAY | 1.6 | 1.6 | 1.0 | 1.0 | 1.6 | 1.6 |
| DBU | — | 0.20 | — | 0.20 | — | 0.20 |
| Viscosity [Pa·s] fresh stored (7 d 60° C.) | 89 85 | 67 64 | 71 77 | 79 96 | 65 59 | 55 51 |
| TFT [min.] | >360 | 270 | 65 | 15 | >360 | 180 |
| SCC: | | | | | | |
| Shore A | 24 | 15 | 23 | 20 | 11 | 9 |
| Tensile strength [MPa] | 0.9 | 0.3 | 0.9 | 0.7 | 0.3 | 0.3 |
| Elongation at break [%] | 155 | 107 | 202 | 202 | 73 | 90 |
| Modulus of elasticity [MPa] | 0.9 | 0.4 | 0.5 | 0.5 | 0.5 | 0.4 |
| 100° C.: | | | | | | |
| Shore A | 20 | 22 | 16 | 16 | 12 | 11 |
| Tensile strength [MPa] | 0.7 | 0.7 | 0.6 | 0.6 | 0.3 | 0.3 |
| Elongation at break [%] | 140 | 142 | 140 | 158 | 73 | 129 |
| Modulus of elasticity [MPa] | 0.4 | 0.6 | 0.5 | 0.5 | 0.4 | 0.2 |

The invention claimed is:

1. A polymer having end groups of the formula (I)

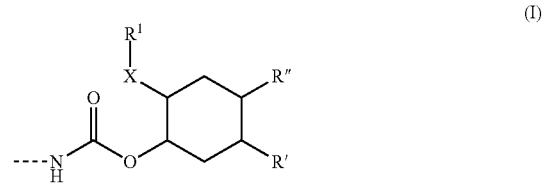

where
either R' is a radical of the formula (II) and R" is a hydrogen radical
or R' is a hydrogen radical and R" is a radical of the formula (II);

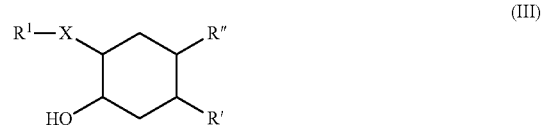

(II)

R¹ is a hydrocarbyl radical which has 1 to 18 carbon atoms and optionally has heteroatoms in the form of ether oxygen, ester oxygen, thioether sulfur or tertiary amine nitrogen;

R² is a linear or branched alkylene or cycloalkylene radical having 1 to 20 carbon atoms, optionally having aromatic components, and optionally having one or more heteroatoms;

R³ is an alkyl radical having 1 to 8 carbon atoms;

R⁴ is an aliphatic or cycloaliphatic or arylaliphatic hydrocarbyl radical which has 1 to 12 carbon atoms and optionally has one or two ether oxygens;

X is O or S; and n is 0 or 1 or 2.

2. A polymer as claimed in claim 1, characterized in wherein R¹ is an aliphatic or cycloaliphatic or arylaliphatic hydrocarbyl radical which has 1 to 12 carbon atoms and optionally has one or two ether oxygens.

3. A polymer as claimed in claim 1, wherein R⁴ is a methyl radical or an ethyl radical.

4. A polymer as claimed in claim 1, wherein X is O.

5. A polymer as claimed in claim 1, wherein X is O and R¹ and R⁴ are each a methyl radical or are each an ethyl radical.

6. A polymer as claimed in claim 1, wherein n is 0.

7. A polymer as claimed in claim 1, wherein it has an average functionality in the range from 1.3 to 4 in relation to end groups of the formula (I).

8. A polymer as claimed in claim 1, wherein it has an average molecular weight in the range from 1'000 to 30'000 g/mol.

9. A polymer as claimed in claim 1, wherein it is a polyether containing silane groups which is liquid at room temperature.

10. A polymer as claimed in claim 1, wherein it is a polyester which is solid at room temperature and/or a polycarbonate which is solid at room temperature.

11. A process for preparing a polymer as claimed in claim 1, wherein at least one hydroxysilane of the formula (III)

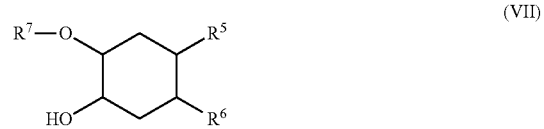

(III)

is reacted with at least one polyurethane polymer containing isocyanate groups.

12. A curable composition comprising at least one polymer as claimed in claim 1.

13. The curable composition as claimed in claim 12, wherein it is applicable at room temperature and is an elastic adhesive or sealant or an elastic coating.

14. The curable composition as claimed in claim 12, wherein it is solid at room temperature and is a hotmelt adhesive.

15. A hydroxysilane of the formula (VII) where

(VII)

either R⁵ is a radical of the formula (VIII) and R⁶ is a hydrogen radical
or R⁵ is a hydrogen radical and R⁶ is a radical of the formula (VIII);

—(CH₂)₂Si(OR⁸)₃   (VIII)

and R⁷ and R⁸ are either each a methyl radical or each an ethyl radical.

* * * * *